Figure 1:
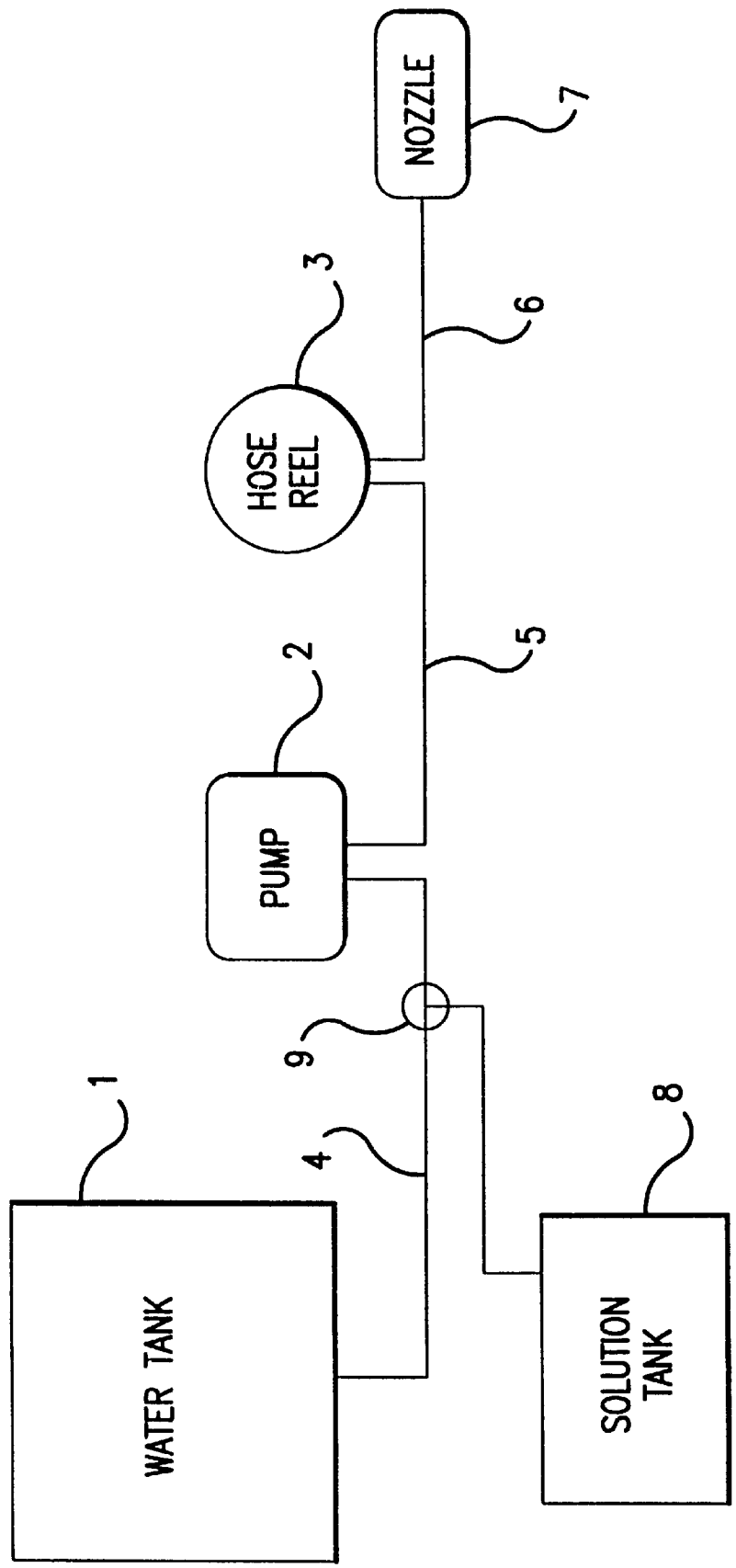

United States Patent
Malavenda et al.

[11] Patent Number: 5,919,731
[45] Date of Patent: Jul. 6, 1999

[54] METHOD FOR CONTROLLING ROOT GROWTH USING DIQUAT BROMIDE

[76] Inventors: Anthony Malavenda, 28 Cross Rd., Dewitt, N.Y. 13224; Kevin Duke, 6976 E. Seneca Turnpike, Jamesville, N.Y. 13078

[21] Appl. No.: 09/064,560

[22] Filed: Apr. 22, 1998

[51] Int. Cl.⁶ .......... A01N 37/34; A01N 43/60; A01N 47/12
[52] U.S. Cl. .......... 504/136; 504/235; 504/300; 504/310
[58] Field of Search .................. 504/136, 235, 504/300, 310

[56] References Cited

U.S. PATENT DOCUMENTS

| | | | |
|---|---|---|---|
| 3,892,588 | 7/1975 | Horne | 71/101 |
| 4,556,434 | 12/1985 | Woogerd | 134/22.14 |
| 5,544,447 | 8/1996 | Easey et al. | 47/66 |

OTHER PUBLICATIONS

Anderson, Wood Powell. Weed Science: Principles and Applications. 3rd ed. West Pub. Co. pp. 178–180, 1996.

*Primary Examiner*—S. Mark Clardy
*Attorney, Agent, or Firm*—Lisa B. Kole

[57] ABSTRACT

The present invention relates to the use of diquat bromide as a root control agent. It is based, at least in part, on the results of green house testing in which application of diquat bromide as a dense foam to tree roots resulted in the destruction of the test roots without causing damage to the upper portion of the trees. Without being bound to any particular theory, it is believed that by applying diquat bromide to produce a high local concentration on the target root, the inactivating effects of local organic substances are overcome, and the diquat bromide kills root tissue by its dessicating activity. The inactivation of diquat bromide by organic materials, under these circumstances, becomes an advantage, as it prevents toxic levels of diquat bromide from traveling downstream from the point of application.

16 Claims, 2 Drawing Sheets

METHOD FOR CONTROLLING ROOT GROWTH USING DIQUAT BROMIDE

1. INTRODUCTION

The present invention relates to a method for controlling root growth comprising applying, to exposed plant roots, an effective amount of diquat bromide. It is based, at least in part, on the discovery that diquat bromide, a herbicide previously used primarily to destroy plant tissue by blocking photosynthesis, is also toxic to root tissue when locally applied. Such methods are particularly useful in reducing the amount of roots present in sewer pipes.

2. BACKGROUND OF THE INVENTION

A number of chemical products have hitherto been used to control vegetative root intrusion in pipeline systems. The most frequently used active ingredients in such products are copper sulfate, corrosive acids or bases, 2,6 dichlorobenzonitrile (hereafter "Dichlobenil") and sodium methyidithiocarbamate (hereafter "Metam"). Each of these products, however, suffer from a number of disadvantages which render their use problematic.

For example, copper sulfate is not detoxified by wastewater treatment plants, where it may either accumulate in the sludge or pass through and contaminate receiving waters. Also, copper sulfate is a systemic herbicide which can damage above-ground vegetation. For these reasons, copper sulfate has fallen into disfavor and its use in many wastewater collection systems is prohibited.

Corrosive acids and bases, such as sulfuric acid, hydrochloric acid, caustic soda, and sulfamic acid, are poured directly into a sewer pipe, where they react with water present in the line to create heat, which burns and kills roots present. Since heat is the primary mechanism of root destruction, these products do little to prevent regrowth and their effectiveness is localized to the point of application. To address some of these problems, certain formulations of corrosives contain copper sulfate or Dichlobenil as additional active ingredients.

Dichlobenil is a common herbicide that acts upon growth points in root systems and therefore provides residual control by deterring regrowth. Because its effectiveness is limited, Dichlobenil is commonly formulated with the active agent Metam.

Metam, and its primary breakdown product MITC, exert their herbicidal action by rupturing plant cell membranes. It has a broad scope of uses, as it is a non-systemic and non-selective herbicide. Metam is a very volatile compound, producing a gas (MITC) when mixed with water; the gas has pesticidal properties and penetrates root growths. It is easy to use in that it is highly soluble in water and is compatible with most foaming agents used for application. Combinations of Metam and Dichlobenil have been found to be so effective, they have virtually replaced other types of active ingredients in the industry. However, several problems associated with Metam have developed which create a motivation to find other suitable herbicides for root control. First, the volatility and toxicity of Metam pose a threat to worker safety. Second, in concentrations typically used for root control, Metam may be toxic to microorganisms at biological wastewater treatment plants, where it may be particularly toxic to nitrifying bacteria. Third, Metam is a marine pollutant, and therefore is not amenable to storm drain applications unless costly precautions are taken to ensure against a release of Metam into fresh water sources such as streams, ponds and lakes.

In contrast to the foregoing agents, the herbicide Diquat has not been contemplated for use in root control. Diquat's primary mode of action is to destroy plant tissue by impairing photosynthesis in the green parts of plants, and is therefore operant on plant tissues that are exposed to light. This mode of action would suggest that Diquat may not damage the roots themselves, but rather enter the plant through the roots and destroy the upper parts of the plant, an undesirable effect. Moreover, the Diquat cation which is responsible for herbicidal action becomes tightly bound to organic substances, upon which it is rendered inactive. In view of the high concentrations of organic substances in soil and sewer pipes, one would have expected that Diquat would be rapidly inactivated and therefore would not be a viable candidate for use in sewers.

3. SUMMARY OF THE INVENTION

The present invention relates to the use of Diquat as a root control agent. It is based, at least in part, on the results of green house testing in which application of Diquat as a dense foam to tree roots resulted in the destruction of the test roots without causing damage to the upper portion of the trees. Without being bound to any particular theory, it is believed that by applying Diquat to produce a high local concentration on the target root, the inactivating effects of local organic substances are overcome, and the Diquat kills root tissue by its dessicating activity. The inactivation of Diquat by organic materials, under these circumstances, becomes an advantage, as it prevents toxic levels of Diquat from traveling downstream from the point of application and may limit its dispersal, in active form, to upper portions of the plant.

Diquat provides other benefits relative to products currently used as root control agents. Diquat is not a marine pollutant and is approved for aquatic use. Diquat is not toxic to fish or other vertebrates at herbicidal concentrations, suggesting that it may be suitable for use in storm drains. Unlike Metam, Diquat is not volatile and therefore is associated with a reduced potential of harmful exposure to workers through inhalation. Diquat is not considered a carcinogen by the USEPA. It has a neutral pH, is compatible with most foaming agents and with Dichlobenil, may be used on all species of plant root, is highly soluble in water, and is non-abrasive. Diquat is effective at application rates as low as five percent of the conventional application rates for Metam, and therefore is associated with lower costs for shipping, packaging, storage and handling.

In a first set of embodiments of the invention, Diquat is applied to exposed roots as a foam in which Diquat is either the sole active agent or one of a plurality of active agents, such as Dichlobenil.

In a second set of embodiments, Diquat may be applied to exposed roots in a pipe via a hydraulic sewer cleaning machine (commercially known as a "Sewer Jet" or "Hydraulic Sewer Cleaning Machine). Such an apparatus pumps water through a hose at high pressure through a nozzle having ports facing rearwards, thereby propelling the Sewer Jet hose down a pipeline, while flushing debris from the pipe. Unlike Metam, which is corrosive to the fittings, tanks, and pumps of the Sewer Jet apparatus, or Dichlobenil, which, because of its insolubility, requires constant agitation to remain in aqueous solution, Diquat is compatible with use in the main tank and pump of the Sewer Jet, without the use of secondary chemical holding tanks, specialized pumps, etc.

Thus, whereas the foaming method for applying Metam requires the use of auxiliary equipment which by-passes the main tank and pump of the Sewer Jet, Diquat may be directly applied via the Sewer Jet as a high pressure spray which not only dispenses the Diquat but also clears away inactivating organic substances. In preferred, non-limiting embodiments of the invention, Diquat may be applied via a hot water or steam delivery system, for example, via a Sewer Jet apparatus.

In another embodiment of the invention, ammonium sulfate may be used to potentiate the effects of Diquat or other root control agents. It has been discovered that when roots were exposed to ammonium sulfate in conjunction with another root control agent, such as Dichlobenil, ammonium sulfate increases the effectiveness of the root control agent in root killing. The primary commercial use of ammonium sulfate is as a fertilizer, an effect which is opposite to the root-killing effect according to the present invention. Further, using traditional ground application methods, the uptake of ammonium sulfate by a root system requires substantial time and varies with soil conditions. Ammonium sulfate has been used to promote the efficacy of certain herbicides by opening stoma on the surface of foliage; as roots lack stoma, any comparable effect on roots would be unexpected. In addition, a tendency of ammonium sulfate to create a foam makes it somewhat undesirable for foliage applications, but is actually advantageous for root control use, e.g., in sewers.

4. DESCRIPTION OF THE FIGURES

FIG. 1. Schematic diagram of Sewer Jet, wherein a water storage tank (1) is linked to a high pressure pump (2) via a suction line (4), and the high pressure pump is able to pump water through a pressure line (5) to a hose reel (3) connected to a high pressure hydraulic sewer cleaner hose (6) having a jet nozzle (7). A solution of root control agent is introduced into the system from a holding tank (8) connected to the suction line (4) via a three-way valve (9).

Figure 2:
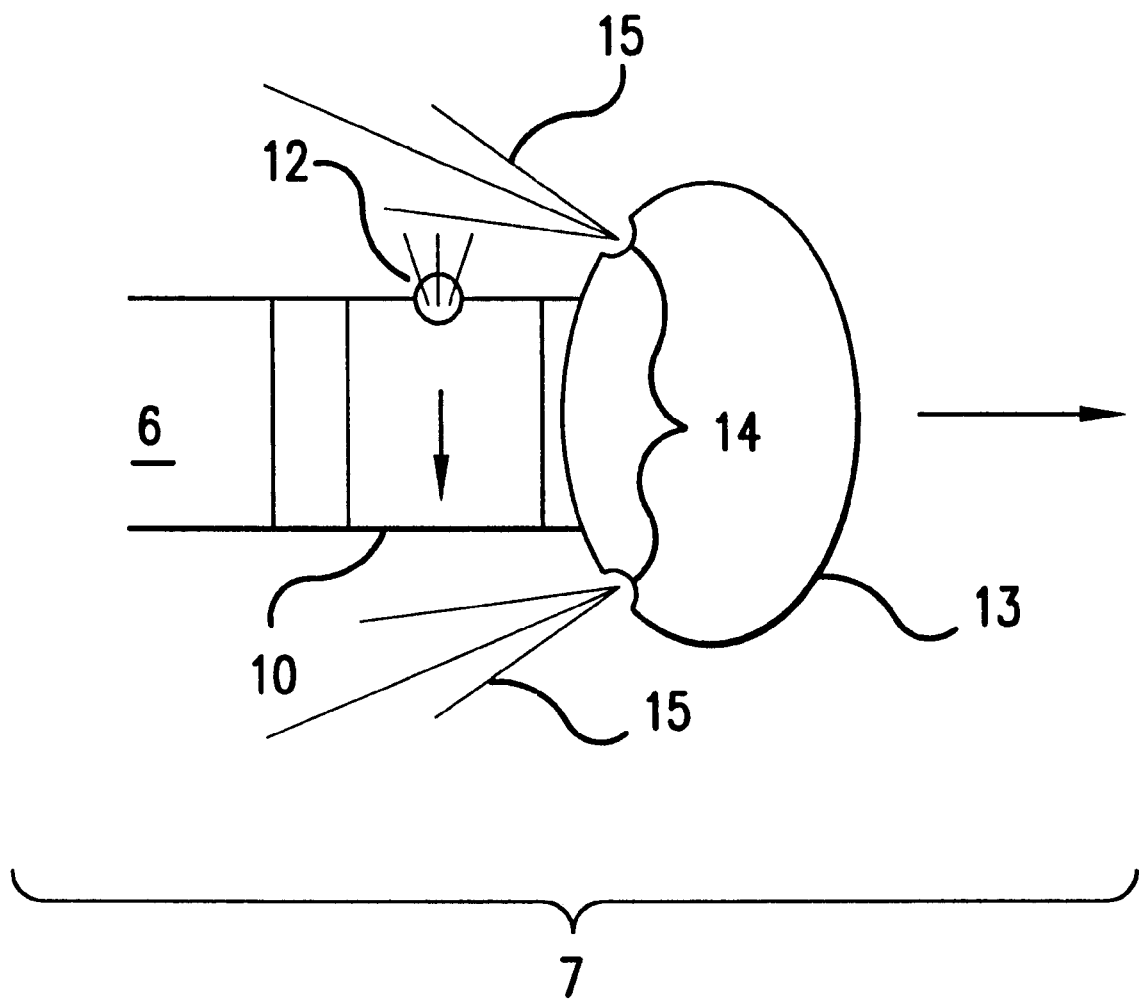

FIG. 2. Expanded view of the jet nozzle referred to in FIG. 1. The nozzle is located at the free end of the high pressure hydraulic sewer cleaning hose (6). It is comprised of a center body (10) that spins in a direction perpendicular to the direction in which the hose is traveling. The center body has one or more side water port (11) that ejects water (12) in a direction that is approximately perpendicular to the direction that the hose is traveling. At the distal end of the nozzle is a stationary portion (13) having multiple rearward facing ports (14) which eject water (15) so as to propel the nozzle and hose forward, in the direction of the large arrow.

5. DETAILED DESCRIPTION OF THE INVENTION

The present invention provides for a method for destroying plant root tissue, comprising applying, to the tissue, an effective amount of diquat bromide ("Diquat"), the technical name of which is 6,7-dihydrodipyrido (1,2-a: 2',1'-c) pyrazinediium dibromide, and which has the chemical structure:

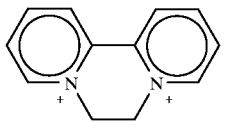

and which is referred to herein as "Diquat". For example, and not by way of limitation, Diquat is sold by Zeneca Inc. as 36.4 percent Diquat and 63.6 percent inert ingredients wherein 2 pounds of Diquat cation per gallon are found in a solution having 3.73 pounds of salt per gallon.

Diquat may be applied, according to the invention, as a solution for application by either pressure spray or foam, whereby the solution comprises between 0.00364 and 0.728 percent Diquat, preferably between 0.00728 and 0.364 percent Diquat, and more preferably between 0.0182 and 0.182 percent Diquat. Such application solutions may be prepared, in nonlimiting examples of the invention, by diluting between 0.01 to 2.0 gallons of Diquat stock aqueous solution (having a concentration of 36.4 percent per gallon, referred to herein as a Diquat stock solution, and intended for further dilution prior to application) per 100 gallons of mixed solution; preferably by diluting between 0.02 to 1.0 gallons of the foregoing Diquat stock solution (36.4 percent) per 100 gallons of mixed solution; and more preferably by diluting 0.05 to 0.5 gallons of Diquat stock solution (36.4 percent) per 100 gallons of mixed solution.

Such solutions, comprising Diquat, may further comprise other agents, such as Dichlobenil, Metam and/or ammonium sulfate, at effective concentrations. Such solutions may also comprise adjuvants which act as carriers, facilitate the removal of organic substances, improve the ability of the active ingredients to adhere or penetrate root tissue, or otherwise improve the efficacy of the treatment, including, but not limited to, detergents, degreasers, emulsifiers, foaming agents, surfactants, wetting agents, penetrants, spreaders, and sticking agents.

In a first set of embodiments, Diquat solution may be applied to exposed roots as a foam, using standard equipment. The most common method of foaming herbicides in sewers, is to mix the herbicide in solution with water and foaming agent. An application hose is placed within the sewer from one manhole, or access point, to another. Compressed air is injected into the stream of mixed solution as it is being pumped, in order to create a foam. The pesticidal foam is then ejected under pressure, filling the sewer as the hose is retrieved.

In preferred embodiments of the invention, Diquat may be used with a cationic or neutral foaming agent. Diquat is typically not compatible with anionic foaming agents, although in test applications a foaming agent having 50% anionic compounds was found to be effective. However, the use of moderately ionic (i.e., 50% or less of the foaming agent components are anionic and the remainder are neutral or cationic) is possible, provided that application takes place promptly after mixing Diquat and foaming agent in solution.

The objective of foam application techniques is generally to fill the pipe with foam as completely as possible as the application hose is being retrieved. The filling capability may be optimized by altering the rate at which the application hose is retrieved. In order to fill a pipe with foam, the application hose may be retrieved at a rate (feet per minute) equal to the gallons of foam generated per minute divided by the volume (gallons per foot of length) of pipe.

As a first specific, nonlimiting example of the invention, typical foaming compounds are associated with an expansion ratio of 20 to 1 when applied via standard sewer foaming equipment. This equipment is normally run at a rate which utilizes 4.5 gallons of solution per minute, which therefore produces 90 gallons of foam per minute (4.5 gallons×20). The volume of an 8 inch diameter pipe is approximately 2.6 gallons per foot of length. At an application rate of 90 gallons of foam per minute in an 8 inch diameter pipe, the hose should be retrieved at a rate of approximately 35 feet per minute (90 gallons/minute÷2.6 gallons per foot=35 feet per minute).

As a second specific nonlimiting example, if a foaming compound provides a lower expansion ratio, e.g., 15 to 1, and the foam application equipment is pumping solution at a lower rate, e.g., 3.5 gallons per minute, then the application hose ejects approximately 53 gallons of foam per minute (3.5×15=53). If the pipe to be treated is 10" in diameter, the volume of said pipe is approximately 4 gallons per foot. The hose retrieval rate in this example would be approximately 13 feet per minute (53 gallons per minute÷4 gallons per foot=13.25).

The flow in large diameter pipes (e.g., 15" and greater) will often overpower the foam such that it cannot fill the pipe and remain in place. This job condition may be handled by applying a 3" to 4" coating of foam along the entire inside circumference of the pipe. The volume of foam required to coat a pipe may be calculated by determining the volume of the pipe to be treated (per foot), and subtracting from that the volume of a pipe 6 to 8 inches smaller in diameter (per foot).

In a second set of nonlimiting embodiments, Diquat solution may be applied to exposed roots in a sewer pipe using a hydraulic sewer cleaning machine (henceforth referred to as a "Sewer Jet") as depicted in FIGS. 1 and 2. The Sewer Jet should be operated using parameters (e.g. pressures and retrieval rates) recommended by the manufacturer. It is advisable to recirculate water within the jet truck in order to ensure an even distribution of Diquat. Several brands and styles of sewer jetting equipment are available, including but not limited to Aquatech, Vac-Con, Vactor, Myers, Clean Earth Machine, and SRECO.

It may be preferable to mix Diquat into an ancillary tank, rather than the primary water tank of the Sewer Jet (see FIG. 1). In this way, fresh water from the primary water tank is used to jet the hose up the pipe, and the Diquat solution in the secondary tank is pumped as the hose is retrieved, by switching off the fresh water tank and switching on the solution tank. Heavy roots and other obstacles may impede the progress of the hose when jetting up a line. This can cause wasteful over-application of chemical in those areas. The applicator should be cautioned to ensure that the Sewer Jet hose has been purged of fresh water and is dispensing Diquat solution before beginning to retrieve the hose.

In preferred embodiments of the invention, a Sewer Jet is equipped with a spinning nozzle, which provides better coverage of the spray solution within the pipe. Typical Sewer Jet nozzles are rearward facing and propel the Sewer Jet hose down a pipe line. The spinning nozzle variant has a side port that jets water in a direction approximately perpendicular to the pipe wall. The jetting action from this side port causes the nozzle body to spin, thereby causing the direction of the spray to rotate, thereby widely distributing sprayed liquid over the inner surface of the pipe. In further preferred embodiments of the invention, a Sewer Jet is equipped with a spray port designed to fog or atomize the spray solution, which minimizes droplet size, and reduces run-off. Fogging sewer jet nozzles and spinning sewer jet nozzles are common stock items for most sewer jet manufacturers.

Steam and/or heated water has been employed as a means to control tree roots in sewers. Such techniques are typically practiced by plugging the downstream end of a sewer and filling it with heated water, or blowing stream through a closed off section of sewer. Controlling roots in sewers with heated water or steam has never achieved commercial success because it is time consuming (each individual root mass must be exposed to the heat source for several minutes), involves substantial energy costs to heat such large volumes of water, and because there is no residual impact that would deter roots from re-growing immediately.

In preferred embodiments of the invention, hot water may be used as a means for delivering Diquat or other herbicides in sewer pipe. It is a desirable medium because, first, hot water has a neutral pH, and it is a natural way to prepare sewer roots for treatment. Hot water spray essentially cleans roots of debris and grease faster and more efficiently than cold water, and/or chemical surfactants. Second, heat accelerates the volatilization of Dichlobenil. Vaporizing Dichlobenil within the pipe significantly increases the penetration of Dichlobenil within root masses. Third, the most potent chemical surfactants for cleaning root masses are anionic. Since water is non-ionic, it provides an effective carrier for Diquat to exposed root tissue. Finally, the herbicidal effect of the heat itself assists the chemical agents to control root growth.

Small sewer jets designed primarily for home lateral sewers usually pump about 4–15 gallons of water per minute. Recently, some manufacturers have added boilers to these machines in order to enhance their cleaning ability. A hot water spray application of Diquat or other herbicide may be performed in the same manner as a normal spray application. Herbicides may be mixed at similar concentrations (for example, see Diquat concentration above) and sprayed in the same manner. The difference is that the water used to produce the spray solution is heated to a temperature of 170 degrees Fahrenheit or more. Higher water temperatures may be used to provide better cleaning, better degreasing, increased herbicide volatilization, and a stronger herbicidal effect.

It should be noted that not all herbicides may be applied using a hot water spray method. The applicator must ensure that the herbicide used is stable at the solution temperature used in this method. Additional volatilization may be desired with some materials, however a transformation to other chemical byproducts, may cause the treatment to be ineffective, and/or unsafe. Increasing the volatilization of herbicides that are already highly volatile may not be desirable. Added volatilization can cause greater worker exposure to such chemicals. It is imperative that the applicator wear respirators and all other safety equipment.

Concentration rates for hot water applications are essentially the same as for normal spray applications described above. Mixing instructions for steam applications are the same as for hot and cold water spray applications. The slower the hose retrieval rate the greater the cleaning and herbicidal impact of the hot water on roots.

Typical hot water sewer jets can produce steam in excess of 300 degrees. Therefore, it is imperative that the herbicides used for treatment do not decompose at such temperatures. A Sewer Jet, set to a steam mode operates at lower pressures (i.e., 300 PSI or less) and volumes (i.e., 2 gallons of water per minute or less). Steam applications may only be performed as the hose is retrieved from the pipe, since there is not sufficient force to propel the sewer hose.

For example, a hot water jet may be used to propel the Sewer Jet hose up a sewer pipe, pumping 4.5 gallons per minute at 3,000 PSI. Once the hose is up the pipe, the boiler may be accelerated to produce steam at approximately 300 degrees, pumping 1.5 gallons of solution per minute, as the hose is retrieved.

In another embodiment of the invention, a solution of ammonium sulfate may be applied to the roots prior to or in conjunction with the application of a root control agent such as Diquat, Dichlobenil, or Metam. In preferred, nonlimiting embodiments, the concentration of ammonium sulfate applied is between 5 to 25 pounds, and preferably 8 to 17 pounds, of ammonium sulfate salt per 100 gallons of water. In one specific nonlimiting embodiment of the invention, the concentration of ammonium sulfate is approximatley one percent (or 10 grams per liter). Methods of application are the same as those set forth above.

6. EXAMPLE

Destruction of Root Tissue by Diquat

Individual branch cuttings of black willow (*Salix nigra*) were collected during the summer (experiment 1) and autumn (experiment 2), and grown in containers according to methods described in Groninger et al., 1997, J. Arboriculture 23: 169–172. In each set of experiments, roots of the cuttings were exposed to a variety of agents and combinations of agents. Each treatment group consisted of 10 and 12 willow cuttings for experiments 1 and 2, respecthree months old grown in experiment 1 were three months old, and those grown in experiment 2 were five months old, at the time of treatment. In both experiments, treatments were applied in a solution of one liter of water and 2% ROUT™ foaming agent (Florida Petrochemicals, Syracuse, N.Y., sold under the names PCO FOAM™ and SEWEROUT-F™) (TABLE 1). Active agents included Metam (Amvac Chemical Corp., 4100 East Washington Blvd., Los Angeles, Calif. 90023, sold under the names VAPAM™ and SEWEROUT-M™) where the percentages in Table 1 reflect volume/volume dilutions of a Metam solution having 32.7 percent active ingredient, Dichlobenil (Uniroyal Chemical, Benson Road, Specialty Products Group, Middlebury, Conn. 06749, sold under the names CASORON™ and SEWEROUT-D™) where the percentages in Table 1 reflect weight/volume dilutions of solid Dichlobenil, FINALE™ (glufosinate, AgrEvo USA Co., Little Falls Center One, 2711 Centreville Road, Wilmington, Del. 19808) where the percentages in Table 1 reflect volume/volume dilutions of an aqueous solution having 120 g solid FINALE™ per liter, GARLON 3A™ (triclopyr, DowElanco, 9330 Zionsville Road, Indianapolis, Ind. 46268) where the percentages in Table 1 reflect volume/volume dilutions of an aqueous solution having 360 g GARLON 3A™ per liter, Rootex (General Chemical Co., P.O. Box 7626, Salem, Oreg., 97303), ammonium sulfate, and Diquat (Zeneca Ag Products, DCC II Wilmington Del. 19897, sold as REWARD™). Following agitation with a foam generator, the treatment solution was poured into an enclosed environment where exposure of roots to the solution was ensured. After twenty minutes, seedlings were returned to trays containing clean water. No effort was made to remove residual treatment solution adhering to exposed roots.

Evaluation of root mortality was conducted one month following treatment using the criteria described by Groninger (supra). Living and dead roots were harvested, dried and weighed for experiment two—three months following treatment.

TABLE 1

| Trt. No. | CHEMICALS (rate) | TREATMENT NAME |
|---|---|---|
| | Experiment 1 | |
| 1 | Metam (4%), Dichlobenil (2.25 g/l) | Metam 1x + Dich. |
| 2 | Metam (3.2%), Dichlobenil (2.25 g/l) | Metam 0.8x + Dich. |
| 3 | Metam (2.4%), Dichlobenil (2.25 g/l) | Metam 0.6x + Dich. |
| 4 | Metam (1.6%), Dichlobenil (2.25 g/l) | Metam 0.4x + Dich. |
| 5 | Metam (0.8%), Dichlobenil (2.25 g/l) | Metam 0.2x + Dich. |
| 6 | Finale (5.8 ml/l), Dichlobenil (2.25 g/l) | Finale 2x + Dich. |
| 7 | Garlon 3A (4.8 ml/l), Dichlobenil (2.25 g/l) | Garlon 2x + Dich. |
| 8 | Dichlobenil (2.25 g/l) | Dich. |
| 9 | — | Control |
| | Experiment 2 | |
| 10 | Metam (4%) | Metam 1x |
| 11 | Metam (3.2%) | Metam 0.8x |
| 12 | Metam (2.4%) | Metam 0.6x |
| 13 | Metam (1.6%) | Metam 0.4x |
| 14 | Rootex (23.4 g/l) | Rootex |
| 15 | Ammonium sulfate (10 g/l), Dichlobenil (2.25 g/l) | Ammonium Sulfate + Dich. |
| 16 | Diquat (2 ml/l) | Diquat 1x |
| 17 | Diquat (20 ml/l) | Diquat 10x |
| 18 | Diquat (2.25 g/l) | Dich. |
| 19 | — | Control |

Results

Threshold concentration of Metam with operational rates of Dichlobenil. All Metam/Dichlobenil mixtures (treatments 1–5) initially killed all roots present at the time of treatment. Regrowth of roots occurred in treatments Metam 0.8x+Dich. (treatment 2) and Metam 0.2x+Dich. (treatment 5). These results suggest that lower rates of Metam plus operational rates of Dichlobenil may be effective in controlling tree roots. Loss of efficacy was evident at rates of Metam below 40% operational concentrations.

Efficacy of Finale, Garlon (Triclopyr) 3A, and Bond in combination with Dichlobenil. Finale and Bond in combination with Dichlobenil resulted in complete mortality of exposed roots but resprouting occurred from roots not directly exposed to herbicide formulations (Table 2). The absence of a detectable effect beyond that of Dichlobenil alone suggests that no improvement over Dichlobenil would be achieved through the use of these chemicals. Garlon 3A caused complete mortality of shoots and does not appear to be suitable for this application.

TABLE 2

Root mortality, shoot mortality and root resprouting for black willow cuttings in response to treatment. All values are expressed in terms of the percent of affected cuttings (n = 10).

| Treatment | Initial exposed root mortality (% of cuttings) | Shoot mortality | Root resprouting following treatment (% of cuttings) | | |
|---|---|---|---|---|---|
| | | | after one mo. | after two mos. | after three mos. |
| Metam 1x + Dich. | 100 | 0 | 0 | 0 | 0 |
| Metam 0.8x + Dich. | 100 | 0 | 0 | 10 | 20 |
| Metam 0.6x + Dich. | 100 | 0 | 0 | 0 | 0 |
| Metam 0.4x + Dich. | 100 | 0 | 0 | 0 | 0 |
| Metam 0.2x + Dich. | 100 | 0 | 0 | 30 | 50 |
| Finale 2x + Dich. | 100 | 0 | 0 | 40 | 60 |
| Garlon 2x + Dich. | 100 | 100 | 0 | 0 | 0 |
| Dich. | 100 | 0 | 0 | 10 | 30 |
| Control | 100 | 0 | NA | NA | NA |

Threshold efficacy of Metam without Dichlobenil. Metam resulted in complete initial mortality of roots at all concentrations tested (TABLE 3). Resprouting of roots occurred in all treatments with the least regrowth occurring at the 1x rate followed by the 0.8x treatment. While a specific threshold concentration was not identified, these results suggest that lowering the concentration of Metam substantially below operational rates will likely not jeopardize the initial efficacy of this chemical. Residual control of root growth by Metam appears to be more sensitive to application rate.

Determination regarding whether ammonium sulfate improves the efficacy of Dichlobenil. Both Dich. and Ammonium Sulfate+Dich. treatments resulted in complete initial control of roots (TABLE 3). However, the combined treatment resulted in 89% fewer roots than Dichlobenil alone. Although complete control of resprouting was not achieved with this treatment, these results suggest that ammonium sulfate may improve the efficacy of Dichlobenil in controlling root resprouting.

Determination of the efficacy of Diquat applied at rates 1 and 10x the cost of Metam. Diquat applied at both 1 and 10x equivalent cost rates for Metam resulted in complete control of treated roots and complete suppression of resprouting roots (TABLE 3). These results suggest that Diquat is more effective in controlling root resprouting than formulations containing Metam or Dichlobenil only. Although formal comparisons between the first and second treatments are not possible, these results suggest that the Diquat 1x rate is comparable to the Metam 1x+Dich. treatment in terms of both initial and residual control of root regrowth. Diquat at the 10x rate resulted in 75 percent shoot mortality while no mortality was observed with the 1x rate.

TABLE 3

Root mortality, shoot mortality and root resprouting for black willow cuttings in response to herbicidal treatment of exposed roots. Root and shoot mortality are expressed as total number of affected cuttings (n = 12)

| Treatment | Initial Exposed Root Mortality | Shoot Mortality | Weight of resprouted roots (g/live cutting) |
|---|---|---|---|
| Metam 1x | 100 | 8 | 0.82 |
| Metam 0.8x | 100 | 0 | 1.05 |
| Metam 0.6x | 100 | 8 | 1.84 |
| Metam 0.4x | 100 | 8 | 1.32 |
| Rootex | 100 | 0 | 2.01 |
| Ammonium sulfate + Dich. | 100 | 0 | 0.21 |
| Diquat 1x | 100 | 0 | 0 |
| Diquat 10x | 100 | 75 | 0 |
| Dich. | 100 | 0 | 1.90 |
| Control | 0 | 0 | 3.47 |

Various publications are cited herein, the contents of which are hereby incorporated by reference in their entireties.

What is claimed is:

1. A method of controlling the growth of an exposed root, comprising applying, to the root, an effective amount of diquat bromide.

2. The method of claim 1, wherein the diquat bromide is applied to the exposed root as a foam.

3. The method of claim 1, wherein the diquat bromide is applied to the exposed root as a spray.

4. The method of claim 3, wherein the spray comprises diquat bromide and hot water.

5. The method of claim 3, wherein the spray is applied to the root by a hydraulic sewer cleaning machine.

6. The method of claim 4, wherein the spray is applied to the root by a hydraulic sewer cleaning machine.

7. A method of controlling the growth of an exposed root, comprising applying, to the root, an effective amount of diquat bromide and a second herbicidal agent selected from the group consisting of methyldithiocarbamate sodium and dichlorobenzonitrile.

8. The method of claim 7, wherein the diquat bromide and second herbicidal agent are applied to the exposed root as a foam.

9. The method of claim 7, wherein the diquat bromide and second herbicidal agent are applied to the exposed root as a spray.

10. The method of claim 9, wherein the spray comprises diquat bromide, a second herbicidal agent and hot water.

11. The method of claim 9, wherein the spray is applied to the root by a hydraulic sewer cleaning machine.

12. The method of claim 10, wherein the spray is applied to the root by a hydraulic sewer cleaning machine.

13. A method of controlling the growth of an exposed root, comprising applying, to the root, an effective amount of ammonium sulfate and an effective amount of a root control agent.

14. The method of claim 13, wherein the root control agent is diquat bromide.

15. The method of claim 13, wherein the root control agent is dichlorobenzonitrile.

16. The method of claim 13, wherein the root control agent is selected from the group consisting of methyldithiocarbamate and methyldithiocarbamate sodium.

\* \* \* \* \*